(12) United States Patent
Lyden et al.

(10) Patent No.: US 8,855,784 B2
(45) Date of Patent: Oct. 7, 2014

(54) IMPLANTABLE MEDICAL DEVICE INCLUDING CONTROLLABLY ISOLATED HOUSING

(75) Inventors: Michael J. Lyden, Shoreview, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 498 days.

(21) Appl. No.: 12/977,141

(22) Filed: Dec. 23, 2010

(65) Prior Publication Data

US 2011/0160807 A1  Jun. 30, 2011

Related U.S. Application Data

(60) Provisional application No. 61/291,713, filed on Dec. 31, 2009.

(51) Int. Cl.
| | | |
|---|---|---|
| *A61N 1/00* | (2006.01) | |
| *A61N 1/02* | (2006.01) | |
| *A61N 1/375* | (2006.01) | |
| *A61N 1/37* | (2006.01) | |
| *A61N 1/39* | (2006.01) | |
| A61N 1/36 | (2006.01) | |

(52) U.S. Cl.
CPC .............. *A61N 1/025* (2013.01); *A61N 1/3605* (2013.01); *A61N 1/3758* (2013.01); *A61N 1/3718* (2013.01); *A61N 1/3956* (2013.01)
USPC ....................................................... 607/63

(58) Field of Classification Search
CPC ....... A61N 1/3718; A61N 1/375; A61N 1/08; A61N 1/36125; A61N 1/025; A61N 1/3956
USPC ................................ 607/4–5, 9, 63, 115–116
See application file for complete search history.

(56) References Cited

U.S. PATENT DOCUMENTS

| | | | |
|---|---|---|---|
| 5,361,776 A * | 11/1994 | Samuelson et al. ........... 600/547 |
| 5,810,802 A * | 9/1998 | Panescu et al. ................. 606/31 |
| 5,916,238 A | 6/1999 | Hauser et al. | |
| 6,516,227 B1 * | 2/2003 | Meadows et al. .............. 607/46 |
| 7,242,981 B2 | 7/2007 | Ginggen | |
| 7,369,898 B1 | 5/2008 | Kroll et al. | |
| 7,561,915 B1 | 7/2009 | Cooke et al. | |
| 7,623,930 B2 | 11/2009 | Zeijlemaker et al. | |
| 2002/0095187 A1* | 7/2002 | Thompson et al. ............... 607/9 |
| 2003/0144705 A1* | 7/2003 | Funke ............................. 607/27 |
| 2006/0167496 A1 | 7/2006 | Nelson et al. | |
| 2006/0293591 A1 | 12/2006 | Wahlstrand et al. | |
| 2007/0191914 A1* | 8/2007 | Stessman ........................ 607/63 |
| 2007/0255332 A1 | 11/2007 | Cabelka et al. | |

(Continued)

*Primary Examiner* — Catherine Voorhees
(74) *Attorney, Agent, or Firm* — Schwegman, Lundberg & Woessner, P.A.

(57) ABSTRACT

An implantable medical device or some other ambulatory medical device, such as a pacer, defibrillator, or other cardiac rhythm management device can include an electrical energy delivery circuit, such as including an integrated circuit comprising a first electrostimulation output terminal, a can terminal, and a switch control output. The ambulatory or implantable device can include at least two switches in series, each including a respective substrate electrically separate from the integrated circuit, and from each other, the switches configured to controllably isolate a conductive housing of the implantable medical device from the can terminal of the integrated circuit, such as in response to the switch control output.

20 Claims, 5 Drawing Sheets

(56) References Cited

U.S. PATENT DOCUMENTS

| | | | |
|---|---|---|---|
| 2008/0079429 A1* | 4/2008 | Gray | 324/318 |
| 2008/0221638 A1* | 9/2008 | Wedan et al. | 607/34 |
| 2009/0088811 A1* | 4/2009 | Wulfman | 607/9 |
| 2009/0149905 A1 | 6/2009 | Lyden et al. | |
| 2009/0149906 A1 | 6/2009 | Ameri et al. | |
| 2009/0149909 A1 | 6/2009 | Ameri | |
| 2009/0157146 A1* | 6/2009 | Linder et al. | 607/60 |
| 2009/0182389 A1* | 7/2009 | Stessman | 607/11 |

\* cited by examiner

IMPLANTABLE MEDICAL DEVICE INCLUDING CONTROLLABLY ISOLATED HOUSING

CLAIM OF PRIORITY

This patent application claims the benefit of priority, under 35 U.S.C. Section 119(e), to Lyden, et al., U.S. Provisional Patent Application Ser. No. 61/291,713, entitled "Implantable Medical Device Including Controllably Isolated Housing," filed on Dec. 31, 2009, which is hereby incorporated by reference herein in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI), is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In an MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement force or torque, heating, induced current or voltage, or one or more other factors. An item known to pose hazards in all MRI environments, such as a ferromagnetic scissors, can be referred to as "MR Unsafe."

Overview

The present inventor has recognized, among other things, that IMDs can include or be coupled to long conductors, such as a leadwire carrying one or more electrostimulation or sensing electrodes contacting a desired tissue region of the patient. For example, the electrodes can be located distally with respect to a housing of the IMD. This can potentially be susceptible to developing a significant MRI gradient induced electromagnetic field (EMF), such as along electrodes located at a distal end of the leadwires and at the IMD case housing its electronics. MRI gradient induced EMF can also exist between significantly separated electrodes. Leadwires and other such elongated conductors included in or coupled to an IMD can also act as antenna, and can therefore also be susceptible to RF emissions from the MRI machine.

Some illustrative examples of IMDs that can include or be coupled to elongated electrical connections to the patient can include, but are not limited to, the following: (1) neuromodulators, such as deep brain stimulators (DBS), various pain control devices, or systems that can stimulate the spinal cord, muscle tissue, or other nerves of the body, e.g., a vagal nerve stimulator (VNS); (2) cardiac pacers; (3) automatic implantable cardioverter defibrillators (AICDs); (3) implantable diagnostic devices such as to monitor cardiac function, e.g., a loop recorder/Holter-monitor-like recording device; or (4) cochlear implants. The present subject matter, such as described in detail herein, can be applied to these and other ambulatory medical devices or IMDs.

This document describes systems, devices, and methods that can include an implantable medical device or some other ambulatory medical device, such as a pacer, defibrillator, or other cardiac rhythm management device, can tolerate magnetic resonance imaging (MRI) or other noise without turning on an integrated circuit diode by selectively isolating one or more internal electronic circuits within the IMD from induced voltage resulting from the MRI or other noise, such as by isolating a housing or "can" of an IMD from the one or more internal electronic circuits.

In an example, an ambulatory or implantable device, such as a pacer, defibrillator, or other cardiac rhythm management device can include an electrical energy delivery circuit, such as including an integrated circuit comprising a first electrostimulation output terminal, a can terminal, and a switch control output. In this example, the ambulatory or implantable device can include at least two switches in series, each including a respective substrate electrically separate from the integrated circuit, and from each other, the switches configured to controllably isolate a conductive housing of the implantable medical device from the can terminal of the integrated circuit, such as in response to the switch control output.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
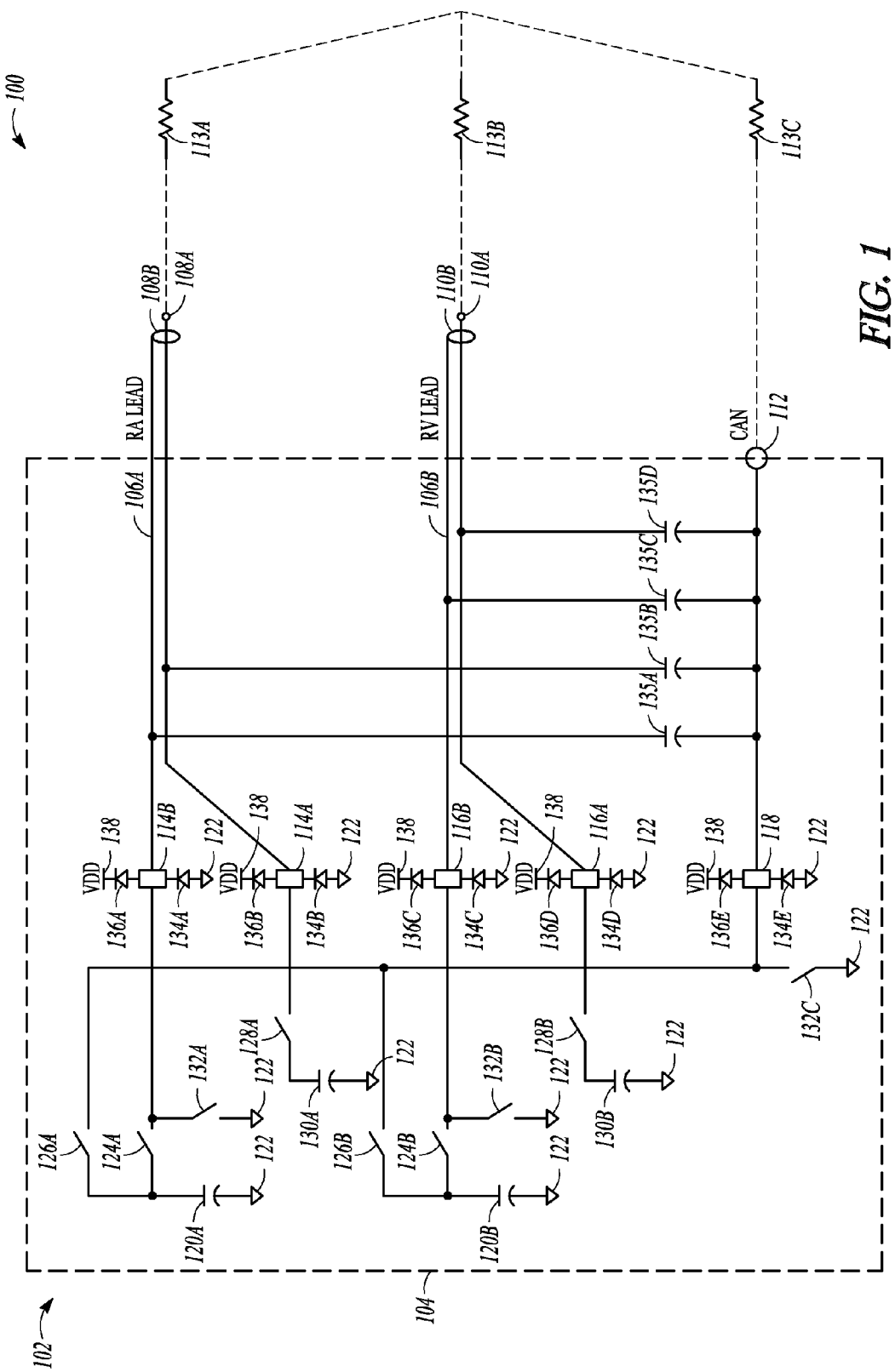
FIG. 1 illustrates an example of portions of a system that can include an implantable or other ambulatory medical device (e.g., an IMD), such as cardiac function management device.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \int_S \int B_1 \cdot dS$$

in which $B_1$ can represent an instantaneous magnetic flux density vector (e.g., in Webers per square meter, or Tesla). If $B_1$ is relatively uniform over the surface S, then the magnetic flux can be approximately $$\Phi_{B1} = |B_1||A|,$$

where A can represent the area of the surface S. Operating MRI equipment can produce a time-varying gradient field having a slew rates in excess of 100 Tesla per second (T/s). The slew rate is the "slope" of the gradient field, $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting electrostimulation therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

This document describes, among other things, systems, devices and methods that can include an ambulatory or implantable device, such as a pacer, defibrillator, or other cardiac rhythm management device, can tolerate magnetic resonance imaging (MRI) or other noise without turning on an integrated circuit diode by selectively isolating one or more internal electrical terminals, such as included as a portion of an integrated circuit, from one or more external conductors, such as a conductive housing or "can" of the IMD.

FIG. 1 illustrates an example of portions of a system 100 that can include an ambulatory or implantable medical device (IMD) 102, such as cardiac function management device. In an example, as explained in more detail below, the IMD 102 can include a pacer, such as for treating bradyarrythmia, with its electrostimulation output circuit contained within an IMD case or housing of an IMD electronics unit 104, which can customarily be implanted in a pectoral region of a patient. In an example, in addition to the IMD 102, the system 100 can include implantable right atrial and right ventricular electrostimulation leads, which can be customarily routed transvenously to the patient's heart. The system 100 can also include other implantable leads, such as a coronary sinus (CS) lead, which can provide one or more electrodes in association with the left atrium or left ventricle.

In an example, the IMD 102 can include an IMD electronics unit 104. The IMD electronics unit 104 can be coupled to one or more electrodes, such as by one or more implantable leads 106 that can be connected to the electronics unit 104. In an example, such leads can include a right atrial (RA) lead 106A and a right ventricular (RV) lead 106B. In an example, the electronics unit 104 can be coupled to one or more electrodes located in association with a left atrium or left ventricle, such as by using a lead that can be introduced into the coronary vasculature, such as via the coronary sinus and great cardiac vein. In an example, the RA lead 106A can include one or more electrodes, such as an RA distal tip electrode 108A and a slightly more proximal RA ring electrode 108B. In an example, the RV lead 106B can include one or more electrodes, such as an RV distal tip electrode 110A and a slightly more proximal RA ring electrode 110B. The IMD electronics unit 104 can include one or more electrodes, such as a can electrode 112 located on a conductive portion of a housing hermetically enclosing the electronics, or a header electrode located on an insulating header extending from the housing. In an example, the IMD electronics unit 104 can also include a communication circuit, such as to communicate with an external local interface device or an external remote interface device, which can also be part of the system 100.

In the example of FIG. 1, the resistors 113A, 113B, and 113C can represent tissue impedances. For example, the impedance between the RA electrodes 108A-B and the RV electrodes 110A-B can be represented by the sum of the tissue resistances of the resistors 113A and 113B; the impedance between the RA electrodes 108A-B and the can electrode 112 can be represented by the sum of the tissue resistances of the resistors 113A and 113C; and the impedance between the RV electrodes 110A-B and the can electrode 112 can be represented by the sum of the tissue resistances of resistors 113B and 113C.

In the example of FIG. 1, the electrodes on the leads can be individually coupled, such as by respective wires in such leads, back to respective terminals in the IMD electronics unit 104. For example, the RA tip electrode 108A can be connected to an RA tip terminal 114A in the IMD electronics unit 104; the RA ring electrode 108B can be connected to an RA ring terminal 114B in the IMD electronics unit 104; the RV tip electrode 110A can be connected to an RV tip terminal 116A in the IMD electronics unit 104; the RV ring electrode 110B can be connected to an RV ring terminal 116B in the IMD electronics unit 104; and the can electrode 112 can be connected (e.g., within the IMD electronics unit 104, rather than via a lead) to a can electrode terminal 118 in the electronics unit 104.

In an example, the IMD electronics unit 104 can include circuitry for generating an electrostimulation energy, storing the electrostimulation energy, and delivering the electrostimulation energy to the tissue of the subject, such as described in Lyden et al. U.S. patent application Ser. No. 12/328,603 entitled "CONFIGURATION OF PACING OUTPUT CHANNELS," which was filed on Dec. 4, 2008, and which published on Jun. 11, 2009 as U.S. Patent Publication No. US-2009-0149905-A1, and which is assigned to Cardiac Pacemakers, Inc., and which is incorporated herein by reference in its entirety, including its description of pacing output channels. For example, an RA electrostimulation voltage can be generated and stored on a first terminal of an RA electrostimulation supply capacitor 120A, the other terminal of which can be connected to a ground reference voltage 122; an RV electrostimulation voltage can be generated and stored on a first terminal of an RV electrostimulation supply capacitor 120B, the other terminal of which can be connected to the ground reference voltage 122.

In an example, a switch can be closed to deliver an RA electrostimulation. For delivering an RA bipolar electro stimulation, this can include selectively connecting the RA electrostimulation supply capacitor 120A to the RA ring terminal 114B, such as by closing the switch 124A during an electrostimulation ("P") clock phase; the return path can be from the RA tip terminal 114A through a switch 128A and a coupling capacitor 130A to the ground reference voltage 122. For delivering an RA unipolar electrostimulation, this can include selectively connecting the RA electrostimulation supply capacitor 120A to the can terminal 112, such as by closing the switch 126A during an electrostimulation ("P") time period; the return path can be from the RA tip terminal 114A through the switch 128A and the coupling capacitor 130A to the ground reference voltage 122.

For delivering an RV bipolar electrostimulation, this can include selectively coupling the RV electrostimulation supply capacitor 120B to the RV ring terminal 116B, such as by closing the switch 124B during an electrostimulation ("P") clock phase; the return path can be from the RV tip terminal 116A through a switch 128B and a coupling capacitor 130B to the ground reference voltage 122. For delivering an RV unipolar electrostimulation, this can include selectively connecting the RV electrostimulation supply capacitor 120B to the can terminal 112, such as by closing the switch 126B during an electrostimulation ("P") time period; the return path can be from the RV tip terminal 116A through the switch 128B and the coupling capacitor 130B to the ground reference voltage 122.

In an example, a delivered electrostimulation can be followed by an opposite polarity recharge pulse, which can be charge-balanced with the electrostimulation pulse, but which need not have the same amplitude as the electrostimulation pulse (e.g., a recharge pulse of lower amplitude and longer duration than the electrostimulation pulse can be used, such as to provide charge balance). For delivering an RA bipolar recharge pulse, a switch 132A can be closed, such as to connect the RA ring terminal 114B to the ground reference voltage 122; the return path can be from the RA tip terminal 114A through the switch 128A and the coupling capacitor 130A to the ground reference voltage 122. For delivering an RA unipolar recharge pulse, a switch 132C can be closed, such as to connect the can terminal 112 to the ground reference voltage 122; the return path can be from the RA tip terminal 114A through the switch 128A and the coupling capacitor 130A to the ground reference voltage 122.

For delivering an RV bipolar recharge pulse, a switch 132B can be closed, such as to connect the RV ring terminal 116B to the ground reference voltage 122; the return path can be from the RV tip terminal 116A through the switch 128B and the coupling capacitor 130B to the ground reference voltage 122. For delivering an RV unipolar recharge pulse, a switch 132C can be closed, such as to connect the can terminal 112 to the ground reference voltage 122; the return path can be from the RV tip terminal 116A through the switch 128B and the coupling capacitor 130B to the ground reference voltage 122.

In the IMD electronics unit 104, certain components can be included on an integrated circuit (IC) chip, while other components can be located off-chip. In an example, off-chip components can include the capacitors 120A-B, 130A-B, and electromagnetic interference (EMI) filter capacitors 135A-D, which can be used to filter unwanted high-frequency noise, such as at the terminals 114A-B, 116A-B, and 118. In an example, the EMI filter capacitors 135A-D can each have a first terminal that can be connected to a respective one of the terminals 114A-B, 116A-B, and can each have a second terminal that can be connected to the terminal 118.

In an example, the switches 124A-B, 126A-B, 128A-B, and 132A-C can be located on the integrated circuit chip, which can input/output (I/O) pads that are electrically connected to the terminals 114A-B, 116A-B, and 118, which, in turn, can be connected to their respective electrodes via respective conductors. In a bulk CMOS n-well semiconductor processing example, on the IC chip, at the I/O pads or at on-chip switches that are respectively connected to the terminals 114A-B, 116A-B, and 118, parasitic IC substrate diodes 134A-E can exist. In such a n-well semiconductor processing example, the parasitic IC substrate diodes 134A-E can include respective cathodes connected at the IC I/O pads corresponding to the respective terminals 114A-B, 116A-B, and 118, and respective anodes commonly connected to the reference voltage to which the IC substrate is connected, such as the ground reference voltage 122. In such an n-well semiconductor processing example, parasitic n-well diodes 136A-E can also exist. In such an n-well semiconductor processing example, the parasitic IC n-well diodes 136A-E can include respective anodes at or connected to the IC I/O pads connected to the respective terminals 114A-B, 116A-B, and 118, and respective cathodes commonly connected to the reference voltage to which the IC n-well is connected, such as the VDD positive power supply reference voltage 138. In an example in which multiple positive power supply reference voltages are provided (e.g., as an illustrative example, a lower VDD=3.0V such as to supply electronic circuitry on the IC, and a higher VCC=12V such as to provide a higher voltage for providing electrostimulation pulses, or for powering a flyback DC-to-DC power converter circuit for generating an even larger defibrillation shock voltage) the diode cathodes can be commonly connected to the higher VCC positive power supply reference voltage, rather than to the lower VDD positive power supply reference voltage.

Figure 2:
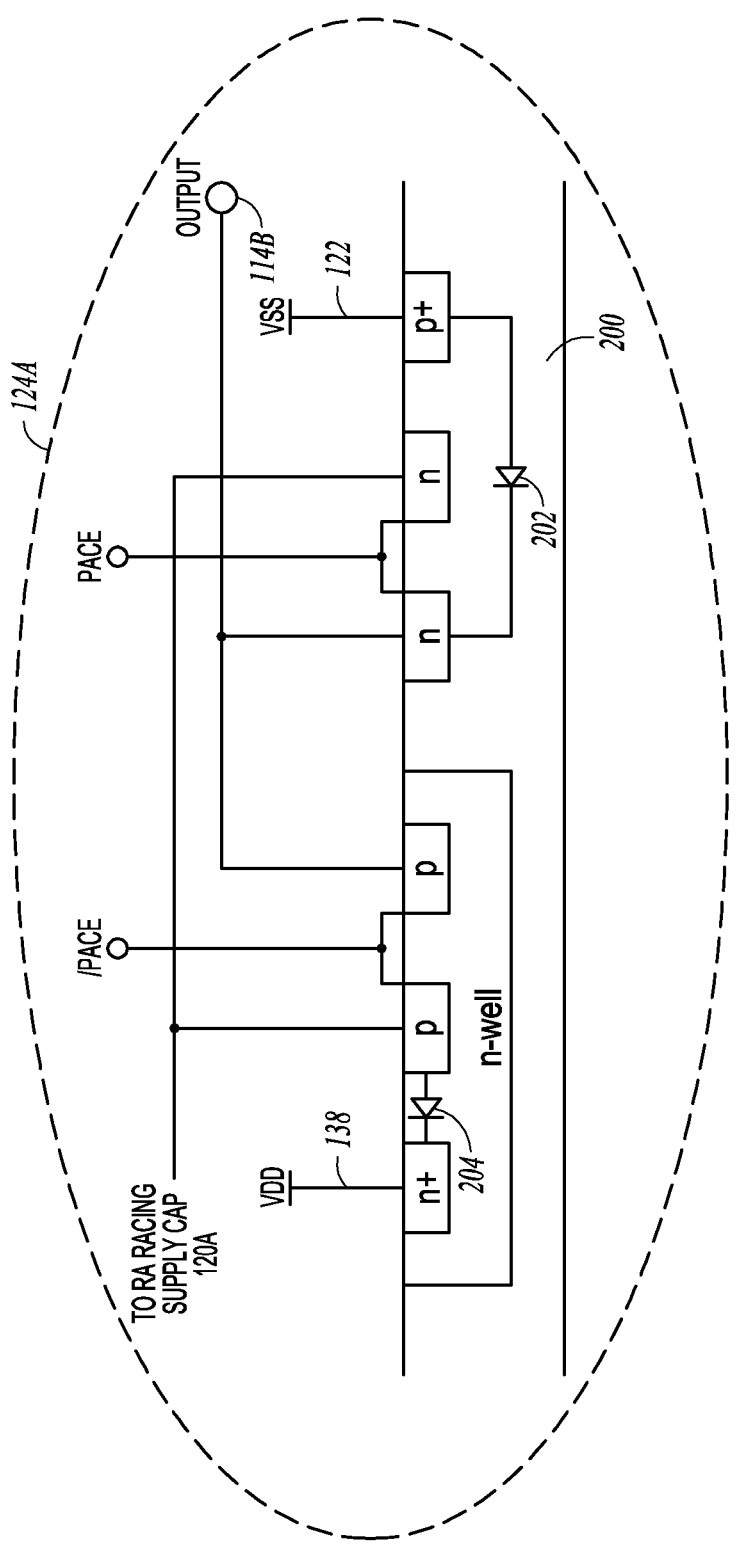
FIG. 2 shows a cross-sectional example of an n-well CMOS implementation of an electrical switch, providing an illustrative example of an IC including an IC parasitic substrate diode and an IC parasitic n-well diode.

FIG. 2 shows a cross-sectional example of an n-well CMOS implementation of switch 124A, providing an illustrative example of an IC 200 including an IC parasitic substrate diode 202 and an IC parasitic n-well diode 204. In an example, unintended current can flow through parasitic substrate or n-well diodes, such as when the output pad voltage at 114B rises above the most positive IC bias voltage (e.g., the VDD positive power supply reference voltage 138) or falls below the most negative IC bias voltage (e.g., the VSS ground reference voltage 122). Upon reviewing FIGS. 1-2, it can become apparent that an analogous situation can arise if the IC uses a p-well bulk CMOS semiconductor process, rather than the n-well bulk CMOS semiconductor process illustrated in the examples of FIGS. 1-2. Although FIG. 2 illustrates the particular example of switch 124A, similar circuit arrangements and considerations can apply to the other IC switches.

Figure 3:
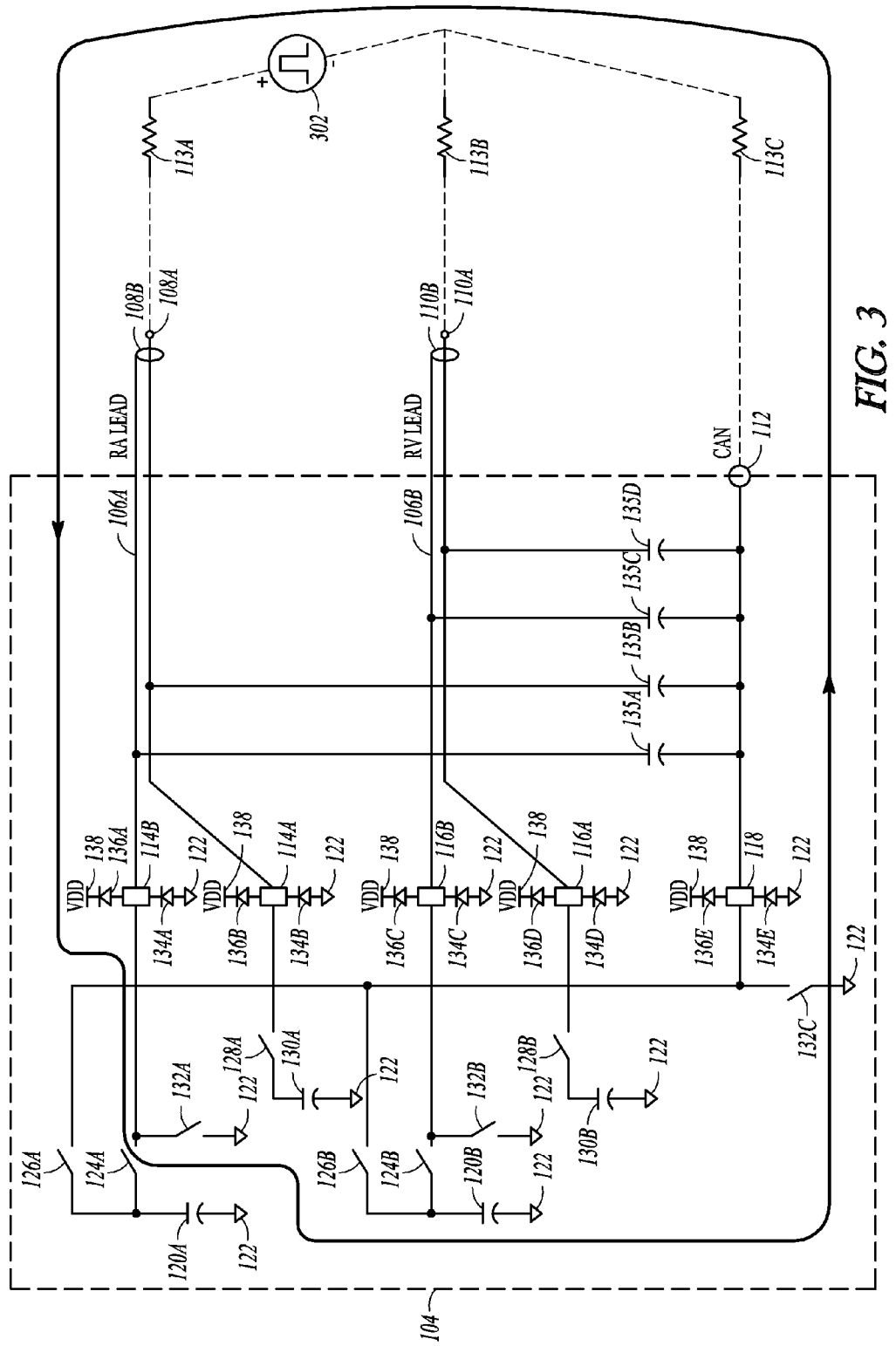
FIG. 3 shows an example illustrating how an EMI external voltage source can cause a voltage to develop, such as between the can electrode and one or more electrodes that are located at the distal end of an electrostimulation lead.

FIG. 3 shows an example illustrating how an EMI external voltage source 302 can cause a voltage to develop, such as between the can electrode 112 and one or more electrodes (e.g., 108A-B, 110A-B) that are located at the distal end of an electrostimulation lead 106. In an example, an electromagnetic field (EMF) can develop along a loop formed by the lead wires en route to their distal electrodes (e.g., 108A-B, 110A-B) and a return ionic conductive tissue path back to the can electrode 112. The EMI source 302 in the example of FIG. 3 can represent one or more of a plethora of possible external interference sources, such as electrocautery, an RF ablation catheter, or induced EMF due to MRI time-varying gradient. In the case of MRI gradient field induction across the leads 106A-B, the EMF voltage can develop along the leads.

In an illustrative cardiac pacer example, there can be up to three leads implanted in the patient, each starting from the IMD electronics unit 104 (e.g., implanted at a subcutaneous pectoral location) and following a similar intravascular trajectory to the heart, with distal portions of the leads terminating in association with respective right atrial (RA), right ventricular (RV), and left ventricular (LV) chambers of the patient's heart. If each such electrostimulation lead follows a similar trajectory, which is typically the case, then the MRI gradient field induced EMF generated between closely spaced electrodes at the distal end of the RA, RV, and LV leads will be very similar. This can result in small, perhaps negligible voltage between the distal end electrodes 108A-B, between 110A-B, or between 108A-B and 110A-B, in some cases. In other cases, it may be possible for a significant (e.g., exceeding a diode forward turn-on voltage of 0.7V) differential voltage to develop between (1) electrodes 108A-B and (2) electrodes 110A-B, such as where RA and RV leads are of differing lead length and excess lead length is coiled in the pocket in which the implantable device electronics unit 104 is implanted. Such a situation can arise not only with a pectorally or abdominally implanted cardiac rhythm management device, but also for other types of ambulatory or implantable medical devices. For example, lead length can be significantly longer in some neurostimulation devices, such as a lumbar spinal cord stimulator, for example, in which a left and right lead trajectory are not constrained by a common conduit as in the case of transvenous approach to the heart.

Moreover, in the example of FIG. 3, a significant large "common mode" voltage can develop between the distal end electrodes 108A-B, 110A-B and the can electrode 112. This common mode voltage can reach several volts. An upper value for the common mode voltage can be estimated by multiplying an estimated largest expected (e.g., mean+3 standard deviations) lead loop area (e.g., 377 cm$^2$, such as identified in a PC-69 cell phone interference example) by the gradient field (dB/dt) of the MRI scanner. For a gradient field (dB/dt) strength of 100 Teslas per second per axis, such as associated with the strongest commercially available 1.5 T and 3.0 T MRI scanners, the resulting upper value for the common mode voltage can be so estimated at about 3.77 Volts.

The IMD electronics unit 104 can include electrostimulation or sensing circuitry that can be selectively coupled to the distal electrodes (e.g., 108A-B, 110A-B). Such circuitry may be subjected to such large common mode voltages. If not properly designed, the MRI-induced resulting common mode voltage may forward-bias semiconductor IC junctions, such as the substrate diode 202, the n-well diode 204, or other pn junctions on the IC. For example, this can occur when the external electrodes are driven by MRI-induced or other interference to a voltage that is above the VDD positive power supply reference voltage 138 or below the VSS ground reference voltage 122.

In an example, when the electrostimulation switches 124A-B or 126A-B, recharge switches 132A-C, and return switches 128A-B are off, the external gradient EMF voltage source 302 does not generate charge or current flow through the substrate of the IC 200 because these circuit paths are blocked by the reverse-biased substrate diode 202 of 134A-E. However, for example, in delivering an RA electrostimulation and recharge, during the RA recharge pulse (e.g., following an RA electrostimulation pulse), the RA recharge switch 132A is closed. The closed RA recharge switch 132A shunts the substrate diode 134A, which is connected to the RA ring electrode 108B being paced and recharged. The MRI-induced voltage source 302 can forward-bias the substrate diode of an electrode not being paced, such as for example the substrate diode 134E associated with the can electrode 112. This can cause the substrate diode 134E to turn on and conduct current, which can flow through the substrate 200, and through the switch 132A, which can return current through the RA ring electrode 108 back to the MRI-induced voltage source 302. In this way, the MRI gradient-induced voltage source 302 can cause current to pass through the can electrode 112 or other electrodes that are intended to be "off."

The magnitude of the unintended substrate currents can depend upon the magnitude of the common mode voltage presented by the MRI-induced voltage source 302 and the exponential current-voltage transfer characteristic of the substrate diodes 202. In an example, the unintended substrate current can exceed the capture threshold for cardiac or neural stimulation. This can transform an intended bipolar electrostimulation or recharge into an unintended unipolar electrostimulation or recharge. In an example, the unintended substrate current can cause an unintended "recharge" of the electrodes intended to be paced. In a similar way, an electrostimulation or recharge in an intended chamber (e.g., RA) can be transformed into an electrostimulation or recharge of an unintended chamber (e.g., RV).

The consequence of an MRI gradient-induced voltage can be an unintended electrostimulation to a cardiac region that was not intended to be stimulated, which can be problematic for a patient. For example, in a dual-chamber (e.g., DOO) electrostimulation mode, this can cause an unintended ventricular electrostimulation accompanying each delivered atrial electrostimulation, together with an intended ventricular electrostimulation with each intentionally-delivered ventricular electrostimulation. This can cause the heart to be paced twice as fast as intended by the programmed electrostimulation rate of the pacer—once during the intended ventricular electrostimulation, and again, unintentionally, during the atrial electrostimulation that is accompanied by the unintended ventricular electrostimulation. In a similar way, the ventricular electrostimulation pulse may cause unintended current to flow via a parasitic substrate diode associated with an atrial distal electrode 108A-B (e.g., causing loss of atrioventricular synchrony) or via a parasitic substrate diode associated with the can electrode 112.

Figure 4:
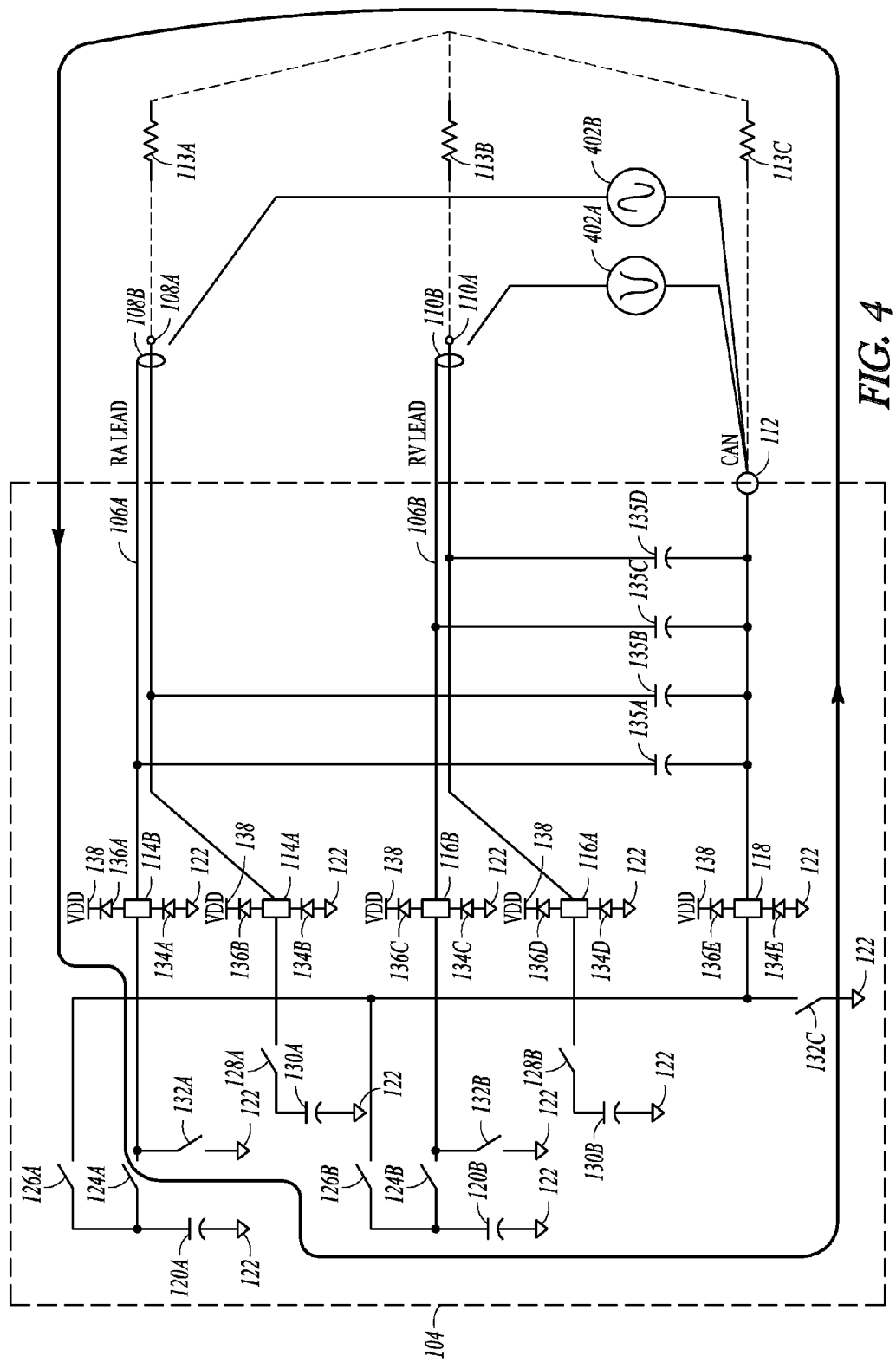
FIG. 4 shows an example of another potential MRI effect that can involve the parasitic substrate diodes: possible rectification of the MRI radiofrequency (RF) field.

FIG. 4 shows an example of another potential MRI effect that can involve the parasitic substrate diodes 202 or well diodes 204 of FIG. 2: possible rectification of the MRI radiofrequency (RF) field. An MRI device can include a powerful pulsed RF field source (e.g., 15-30 kW), which can be used to process the patient's hydrogen atom nuclei spins during MRI scanning of the patient. During each RF pulse, an electric field (E-field) can form, such as tangentially along the leads 106A-B that are connected to the IMD electronics unit 104. This can produce RF currents in the conductors in the leads 106A-B. The resulting MRI RF-induced currents in the leads 106A-B can cause a voltage 402A-B to develop across an EMI capacitor 135A-D, such as shown in the example of FIG. 4. Variations in lead length, lead orientation or trajectory, and MRI RF-induced tangential E-field can generate differences in phase between the voltage 402A and the voltage 402B, such as illustrated in the example of FIG. 4.

Generally, the EMI filter capacitors 135A-D can shunt lead current to the conductive case, housing the IMD electronics unit 104, which is connected to the can electrode 112. This can help protect the electronic circuitry internal to the IMD electronics unit 104 from external interference. It is desirable that the EMI filter capacitors 135A-D should keep the voltage difference between the various lead electrodes (e.g., 108A-B and 110A-B) and the can electrode 112 negligibly small. However, the RF voltage appearing across the EMI capacitors 135A-D, which is a function of the impedance of the EMI filter capacitors 135A-D and the magnitude of the RF currents in the leads 106A-B can, in certain circumstances (e.g., in an MRI setting) become significant. Parasitic inductance along the connections to the EMI filter capacitors 135A-D and the can electrode 112 can also contribute to developing a voltage across the connections of the housing feedthroughs (e.g., extending through the conducting housing of the IMD electronics unit 104, helping provide electrical connections from respective external terminals connected to the leads to corresponding internal terminals connected to IC circuitry in the IMD electronics unit 104. This can expose the electronic circuits within the IMD electronics unit 104 to unintended activation of (and rectification by) substrate diodes, such as in a similar manner to that discussed above for the MRI gradient-induced voltages and resulting currents.

In the example of FIG. 4, for convenience and ease of understanding, the distributed RF antenna pickup of the lead can be simplified and represented as a lumped circuit element, e.g., such as by representing the situation using a voltage source of arbitrary phase at a distal end of the lead, such as can be associated with the patient's heart. In reality, the radiated electric field pick-up and propagation of current or voltage down the lead is a more complicated phenomenon that can be represented and solved more accurately, such as by using a computerized electromagnetic field solver. The RF voltage that can develop between the internal (e.g., within the housing of the IMD electronics unit 104) connections to a lead electrode and to the can electrode 112 can be characterized as the product of the RF current flowing through the proximal side of the patient lead and the input reactance of the EMI filter capacitor 135 to the can electrode 112. Generally, the proximal side (near the housing of the IMD electronics unit 104) RF lead current can depend more on the lead length, internal construction and its component geometry and its resulting distributed impedance than on the proximal end termination impedance over a wide range of capacitance values of the EMI capacitors 135. If the IMD 102 does not employ EMI filter capacitors 135, then the RF voltage that develops between the various lead connections of the IMD electronics unit 104 and the housing connection 118 or can electrode 112 can depend on the input impedance that the electronics within the IMD electronics unit 104 present to the patient lead system.

If MRI gradient-induced EMF or the MRI RF or other RF induced voltage exceed the forward turn-on voltage of the IC parasitic substrate or electrical switch diodes, then unintended low frequency currents may flow, such as between a heart electrode and the can electrode 112, or potentially between distal heart or other patient electrodes. A possible effect of such an unwanted current, such as when the IMD 102 comprises a cardiac pacer, may include unintended cardiac electrostimulation.

Figure 5:
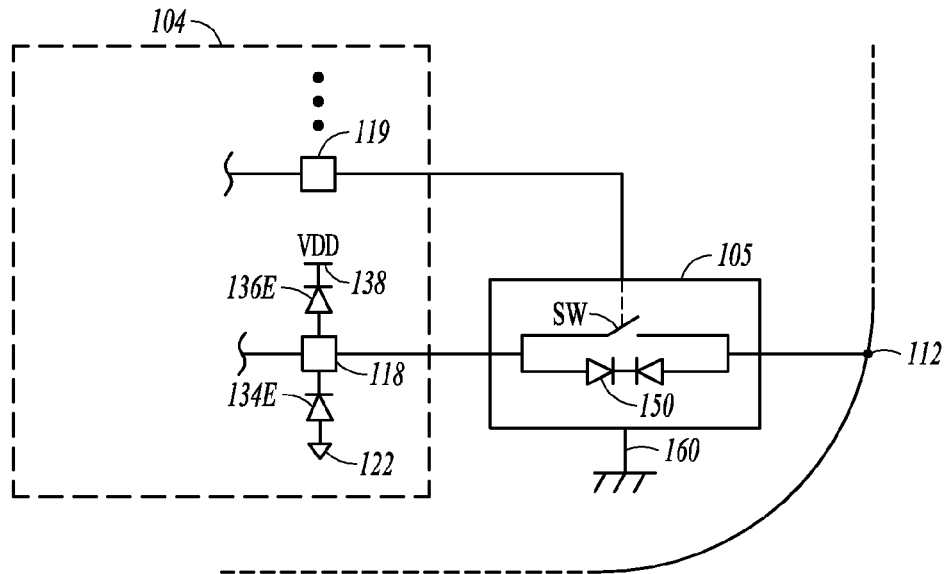
FIG. 5 shows an example of a solution that can help reduce or avoid such MRI gradient-induced and MRI RF-induced effects, such as rectification effects.

FIG. 5 shows an example of a solution that can help reduce or avoid such MRI gradient-induced or MRI RF-induced effects, such as rectification effects. In the example of FIG. 5, a switch can be used, such as to avoid the undesired rectification of MRI or other external EMI sources by the electronic circuitry within a first IMD electronics unit 104. The switch can be used such as for isolating a housing or "can" 112 of the IMD from a can electrode terminal 118, such as included as a portion of an integrated circuit, integrated module, or other device package located within the IMD. Although FIG. 5 is illustrated, for conceptual clarity, with respect to the electrostimulation output circuitry of FIGS. 1-4, such a housing isolation technique can be applied to a neural stimulation circuit's current output circuitry or other IMD electronics of other types of IMDs, or to one or more other electrode terminals, such as when the one or more other electrode terminals are not needed.

In FIG. 5, the can electrode terminal 118 can be connected to a VSS ground reference voltage 122, such as via substrate diode 134E, or to a VDD positive power supply reference voltage 138, or one or more other positive power supply references, such as through a parasitic diode 136E (e.g., in an n-well CMOS integrated circuit processing example). In an example, the can electrode terminal 118 can be controllably isolated from the can 112 of the IMD such as by using a second electronics unit 105, such as including a switch circuit SW and a blocking diode 150. In an example, the state of the switch circuit SW can be controlled using a switch control output 119 of the first electronics unit 104. In an example, a substrate 160 or other portion of the second electronics unit 105 can be kept electrically separated from the first electronics unit 104, such as except for the switch control output 119, can electrode terminal 118, and can 112 connection.

In an example, the switch SW can include one or more types of components or devices, such as one or more NMOS, PMOS or junction field-effect transistors (FETs), one or more insulated gate bipolar transistors (IGBTs), one or more bipolar junction transistors (BJTs), or one or more other mechanical switches (e.g., a relay, a microelectromechanical device, etc.) or solid-state switches.

In an example, the IMD can include an MRI mode of operation that can be user-programmed, such as prior to MRI scanning of a patient. In an example, the MRI mode of operation can be automatically entered, such as in response to a sensor (e.g., Hall effect sensor, an inductor saturation detector, or the like) in the IMD electronics unit 104 detecting the presence of a magnetic field such as associated with an MRI scanner. In an example, the IMD can revert or change from an MRI mode of operation back to a normal or ambulatory mode of operation, such as in response to information from the sensor indicating that the magnetic field has diminished or disappeared.

In an example, in the MRI mode, the switch SW can be opened, isolating the can 112 from the can electrode terminal 118. In an example where the switch SW is opened, unipolar sensing or electrostimulation can be precluded since the can 112 is electrically isolated from the first electronics unit 104. However, when the switch SW is opened, an unwanted EMF or rectified potential can also be prevented from coupling to the first electronics unit 104 since blocking diode 150 breaks a potential EMI or EMF coupling loop including the can 112. In an example, the blocking diode 150 can provide additional protection to prevent forward biasing of the diodes 134E, 136E, or coupling of RF voltages or currents to the can electrode terminal 118 or one or more other terminals such as discussed in FIGS. 1-4. In an example, the blocking diode 150 can include multiple diode structures, such as including two or more individual diode structures, such as in an anode-to-anode or cathode-to-cathode configuration, as shown in FIGS. 5-6.

In an example, it can be preferable to generally always operate in the external EMI protection mode (e.g., the "MRI mode"). This can avoid having to switch back and forth between "normal mode" and "MRI mode," such as by eliminating any connection between the can 112 and the first electronics unit 104. However, unipolar electrostimulation or sensing can sometimes be desired, and such unipolar electrostimulation or sensing can be precluded when the switch SW is always open, or when the connection between the can 112 and the first electronics unit 104 is entirely omitted. In an example, the switch SW can be controlled to remain open, isolating the can 112, except during delivery of a unipolar electrostimulation or recharge pulse wherein the intended electrostimulation or recharge pulse electrodes includes using the can 112.

Figure 6:
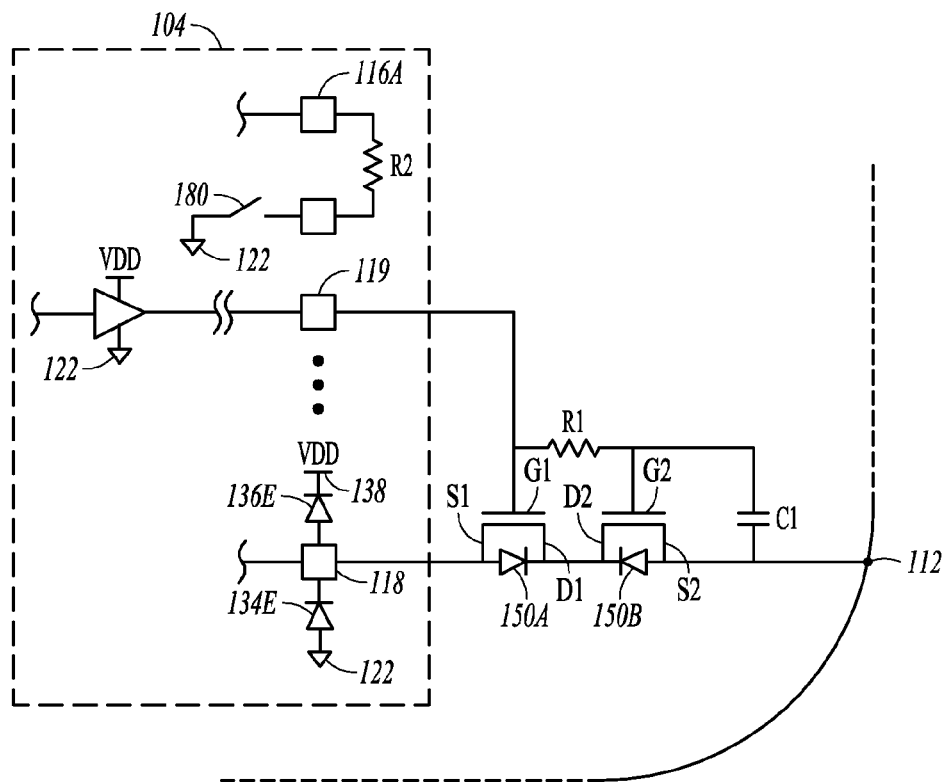
FIG. 6 shows another example of a solution that can help reduce or avoid such MRI gradient-induced and MRI RF-induced effects.

FIG. 6 shows an example of a solution that can help reduce or avoid such MRI gradient-induced and MRI RF-induced effects. In the example of FIG. 6, two or more switches can be introduced, such as to provide enhanced isolation between a can electrode terminal 118 included in a first electronics unit 104, and a housing or "can" 112 of an IMD, such as to avoid the undesired rectification of MRI or other external EMI sources by the electronic circuitry within the IMD electronics unit 104. Although FIG. 6 is illustrated, for conceptual clarity, with respect to a portion of the electrostimulation output circuitry of FIGS. 1-4, such a multiple-switch technique can be applied to a neural stimulation circuit's current output circuitry or other IMD electronics of other types of IMDs, or to one or more other electrode terminals, such as when the one or more other electrode terminals are not needed.

In FIG. 6, the can electrode terminal 118 can be connected to a VSS ground reference voltage 122, such as via substrate diode 134E, or to a VDD positive power supply reference voltage 138, or one or more other positive power supply references, such as through a parasitic diode 136E (e.g., in an n-well CMOS integrated circuit processing example). In an example, the can electrode terminal 118 can be controllably isolated from the can 112 of the IMD such as by using a combination of multiple switches, such as including a first switch SW1, a second switch SW2, a first blocking diode 150A, and a second blocking diode 150B.

In an example, one or more of switches SW1-2 can include one or more NMOS, PMOS or junction field-effect transistors (FETs), one or more insulated gate bipolar transistors (IG-BTs), one or more bipolar junction transistors (BJTs), or one or more other mechanical (e.g., a relay, a microelectromechanical device, etc.) or solid-state switches. In the example of FIG. 6, the switches SW1-2 can be respective FETS, and the respective blocking diodes 150A-B can be respective body diodes of the respective FETS. For example, a source terminal S1 of the switch SW1 can be connected to the can electrode terminal 118. A drain terminal D1 of the switch SW1 can be connected to a corresponding drain terminal D2 of the switch SW2. In an example, the body diode 150B of the switch SW2 opposes the polarity of the body diode 150A of the switch SW1. In an example, a source terminal S2 of the switch SW2 can be connected to the can 112 of the IMD.

In an example, the state of one or more of switches SW1-2 can be controlled using a switch control output 119 of the first electronics unit 104. In an example, a gate G1 of the first switch SW1 can be directly driven by an output of the first electronics unit 104, such as an integrated circuit output from an analog or mixed-mode integrated circuit, such as driven by an output circuit 170. In an example, a gate G2 of the second switch SW2 can also be driven by the switch control output 119, but isolated through an isolation resistor R1 between the first and second gates G1-2. In an example, a capacitor C1 can be connected to the second gate G2, such as to preserve a specified gate-to-source (e.g., G2 to S2) bias condition, such as when transient EMF or EMI voltages drive the can 112 voltage up or down with respect to VSS 122. Thus, the transient can 112 voltage can be "held off." A ground referencing resistor R2 (e.g., 100 KΩ) and series switch 180 can be included in the electrostimulation output circuitry, such as between an electrostimulation electrode terminal 116A and VSS 122. The switch 180 can be closed, when not delivering an electrostimulation or recharge, such as to selectively connect the electrostimulation electrode terminal 116A, among other terminals, to VSS 122. This resistor R2 can help maintain a quiescent common-mode operating voltage at the electrostimulation electrode terminal 116A, and similar resistors and switches can be used with respect to the other terminals of the IMD electronics unit 104, such as to help maintain their respective quiescent common mode operating voltages.

Note, however, that in applications in which it is possible that the external EMF (e.g., a combined gradient and RF induced EMF) exceeds the stand-off voltage afforded by the switches SW1-2, or diodes 150A-B, it may be preferable not to close the switch 180 associated with the referencing resistor R2 between intended output electrostimulation therapy pulses, such as to avoid even the small amount of rectified current through the series resistor R2 in the loop that it forms with the parasitic diode, as described above. Without such a resistor R2, the respective lead electrode voltages may "float" to any voltage between the negative power supply rail value (e.g., ground) and the positive power supply rail value (e.g., a VDD=12V protection supply for the electrostimulation switches 124A-B or 126A-B and the recharge switches 132A-C, such as shown in FIG. 1). In an example, the resistor R2 can be selectively switched to the VSS ground reference voltage 122 during normal operation (e.g., by also closing the switch 180) or when the IMD is placed in an "MRI mode" of operation.

In an example, a respective substrate or other portion of the first and second switches SW1-2 can be kept respectively isolated, such as providing electrical isolation between switches SW1-2, and between each respective switch SW1 or SW2 and the first electronics unit 104. For example, respective substrate electrical isolation between the first electronics unit 104 and the first or second switches SW1 or SW2 can prevent a current from a gradient-induced EMF from circulating between one or more terminals of SW1 or SW2, such as via a commonly shared substrate.

Various Examples and Notes

Example 1 includes subject matter (such as an apparatus) comprising an implantable medical device, including an implantable housing including a conductive portion, an implantable electrostimulation output circuit located within the housing, the electrostimulation output circuit including a housing terminal and a switch control output, and a switch, physically separate from the electrostimulation output circuit, located within the housing, and electrically coupled between the housing terminal and the conductive portion of the housing, the switch configured to controllably electrically isolate the conductive portion of the housing from the housing terminal of the electrostimulation output circuit in response to a control signal provided by the switch control output.

In Example 2, the subject matter of Example 1 can optionally include a rectifier electrically coupled in parallel with the switch, between the housing terminal of the electrostimulation output circuit and the conductive portion of the housing.

In Example 3, the subject matter of one or any combination of Examples 1-2 can optionally include an electrostimulation output circuit comprising an integrated circuit including a first substrate, the switch comprising a second substrate, and the first and second substrates are electrically isolated from each other.

In Example 4, the subject matter of one or any combination of Examples 1-3 can optionally include a switch comprising two transistors electrically coupled in a series configuration and configured to be respectively controlled via the switch control output to controllably electrically isolate the conductive portion of the housing from the housing terminal of the electrostimulation output circuit.

In Example 5, the subject matter of one or any combination of Examples 1-4 can optionally include two transistors comprising field effect transistors, and each field effect transistor including a respective body diode in parallel with a respective source and a respective drain terminal of each field effect transistor; and wherein the field effect transistors are electrically coupled in a series configuration wherein the body diodes oppose each other.

In Example 6, the subject matter of one or any combination of Examples 1-5 can optionally include an electrostimulation output circuit comprising a substrate, each transistor including a respective substrate, and the respective substrates of the transistors are respectively electrically isolated from the electrostimulation output circuit substrate, and from each other.

In Example 7, the subject matter of one or any combination of Examples 1-6 can optionally include two transistors comprising a first transistor electrically coupled to the housing terminal of the electrostimulation output circuit, a second transistor electrically coupled to the conductive portion of the housing, the first and second transistors connected to each other in a series configuration, the second transistor including a control input, and the implantable medical device including a capacitor connected between the control input of the second transistor and the conductive portion of the housing.

In Example 8, the subject matter of one or any combination of Examples 1-7 can optionally include a first transistor comprising a control input, and the implantable medical device includes a first resistor connected between the respective control inputs of the first and second transistors.

In Example 9, the subject matter of one or any combination of Examples 1-8 can optionally include an electrode at a location distal to the housing, the electrode coupled to the first electrostimulation output terminal, the implantable medical device comprises a second resistor connected between the first electrostimulation output terminal and a circuit ground of the electro stimulation output circuit, and the apparatus is configured to charge the capacitor using a current path including the first resistor, the second resistor, the distally-located electrode, and the conductive portion of the housing to maintain a specified voltage between the control input of the second transistor and a terminal of the second transistor connected to the conductive portion of the housing.

In Example 10, the subject matter of one or any combination of Examples 1-9 can optionally include a magnetic field sensor, and the electrostimulation output circuit is configured to controllably isolate the conductive portion of the housing from the housing terminal of the electrostimulation output circuit using the switch in response to information from the magnetic field sensor indicative of at least one of a magnetic resonance imaging field or another external magnetic field in excess of a specified threshold.

In Example 11, the subject matter of one or any combination of Examples 1-10 can optionally include an electro stimulation output circuit configured to controllably isolate the conductive portion of the housing from the housing terminal of the electrostimulation output circuit in response to a command received from an external assembly in communication with the implantable medical device.

Example 12 can include, or can optionally be combined with the subject matter of one or any combination of Examples 1-11 to include, subject matter (such as a method, a means for performing acts, or a machine-readable medium including instructions that, when performed by the machine, cause the machine to perform acts) comprising controllably isolating a conductive portion of a housing of the implantable medical device from a housing terminal of an implantable electrostimulation output circuit included as a portion of the implantable medical device, using a switch located within the housing, the switch physically separate from the electrostimulation output circuit.

In Example 13, the subject matter of Example 12 can optionally include using a magnetic field sensor, and controllably isolating the conductive portion of the housing from the housing terminal of the electrostimulation output circuit using the switch, in response to information from the magnetic field sensor indicative of at least one of a magnetic resonance imaging field or another external magnetic field in excess of a specified threshold.

In Example 14, the subject matter of one or any combination of Examples 12-13 an optionally include allowing the conductive portion of the housing to be connected to the housing terminal of the electrostimulation output circuit via the switch, in response to information from the magnetic field sensor indicative that the external magnetic field is below the specified threshold, during a specified duration of time.

In Example 15, the subject matter of one or any combination of Examples 12-14 can optionally include connecting the conductive portion of the housing to the housing terminal of the electrostimulation output circuit via the switch, by default, when the information received from the magnetic field sensor indicates that the external magnetic field is below the specified threshold.

In Example 16, the subject matter of one or any combination of Examples 12-15 can optionally include controllably isolating the conductive portion of the housing from the housing terminal of the electrostimulation output circuit using the switch, in response to a command received from an external assembly in communication with the implantable medical device.

In Example 17, the subject matter of one or any combination of Examples 12-16 can optionally include using an electrostimulation output circuit comprising an integrated circuit including a first substrate, the switch including a second substrate, and the first and second substrates are electrically isolated from each other.

In Example 18, the subject matter of one or any combination of Examples 12-17 can optionally include using a switch comprising two transistors electrically coupled in a series configuration, and controllably electrically isolating the conductive portion of the housing from the housing terminal of the electrostimulation output circuit using the two transistors.

In Example 19, the subject matter of one or any combination of Examples 12-18 can optionally include using two transistors comprising field effect transistors, each field effect transistor including a respective body diode in parallel with a respective source and a respective drain terminal of each field effect transistor, and the field effect transistors electrically coupled in a series configuration wherein the body diodes oppose each other.

Example 20 includes subject matter (such as an apparatus) comprising an implantable medical device including an implantable housing having a conductive portion, an implantable electrostimulation output circuit located within the housing, the electrostimulation output circuit including a housing terminal and a switch control output, and a switch comprising two transistors electrically coupled in a series configuration, the switch physically separate from the electrostimulation output circuit and located within the housing, and electrically coupled between the housing terminal and the conductive portion of the housing, the switch configured to controllably electrically isolate the conductive portion of the housing from the housing terminal of the electrostimulation output circuit in response to a control signal provided by the switch control output. In Example 20, the electrostimulation output circuit includes a substrate, each transistor includes a respective substrate, the respective substrates of the transistors are respectively electrically isolated from the electrostimulation output circuit substrate, and from each other.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
an implantable medical device comprising:
an implantable housing including a conductive portion;
an implantable electrostimulation output circuit located within the housing, the electrostimulation output circuit including:
one or more reference voltages coupled to a respective diode;
a can electrode terminal configured to be controllably connected to the conductive portion of the housing, the can electrode terminal configured to be connected to the one or more reference voltages each via the respective diode; and
a programmable switch control signal generator circuit configured to generate a control signal in response to one or more of a user-programmed magnetic resonance imaging (MRI) mode or in response to a detected magnetic field in excess of a specified threshold and to output the control signal using a switch control output; and
a switch, physically separate from the electrostimulation output circuit, located within the housing, and electrically coupled between the can electrode terminal and the conductive portion of the housing, the switch configured to controllably electrically isolate the conductive portion of the housing from the can electrode terminal of the electrostimulation output circuit in response to the control signal provided by the switch control output.

2. The apparatus of claim 1, comprising a rectifier electrically coupled in parallel with the switch, between the can electrode terminal of the electrostimulation output circuit and the conductive portion of the housing.

3. The apparatus of claim 1, wherein the electrostimulation output circuit comprises an integrated circuit including a first substrate;
wherein the switch includes a second substrate; and
wherein the first and second substrates are electrically isolated from each other.

4. The apparatus of claim 1, wherein the switch comprises two transistors electrically coupled in a series configuration and configured to be respectively controlled via the switch control output to controllably electrically isolate the conductive portion of the housing from the can electrode terminal of the electrostimulation output circuit.

5. The apparatus of claim 4, wherein the two transistors comprise field effect transistors;
wherein each field effect transistor includes a respective body diode electrically coupled between a respective source and a respective drain terminal of each field effect transistor; and wherein the field effect transistors are electrically coupled in a series configuration wherein the body diodes oppose each other.

6. The apparatus of claim 4, wherein the electrostimulation output circuit includes a substrate;
wherein each transistor includes a respective substrate, and
wherein the respective substrates of the transistors are respectively electrically isolated from the electrostimulation output circuit substrate, and from each other.

7. The apparatus of claim 4, wherein the two transistors comprise:
a first transistor electrically coupled to the can electrode terminal of the electrostimulation output circuit;
a second transistor electrically coupled to the conductive portion of the housing;
wherein the first and second transistors are connected to each other in a series configuration;
wherein the second transistor includes a control input; and
wherein the implantable medical device includes a capacitor connected between the control input of the second transistor and the conductive portion of the housing.

8. The apparatus of claim 7, wherein the first transistor includes a control input; and
wherein the implantable medical device includes a first resistor connected between the respective control inputs of the first and second transistors.

9. The apparatus of claim 8, further comprising an electrode at a location distal to the housing, the electrode coupled to the first electrostimulation output terminal;
wherein the implantable medical device comprises a second resistor connected between the first electrostimulation output terminal and a circuit ground of the electrostimulation output circuit; and
wherein the apparatus is configured to charge the capacitor using a current path including the first resistor, the second resistor, the distally-located electrode, and the conductive portion of the housing to maintain a specified voltage between the control input of the second transistor and a terminal of the second transistor connected to the conductive portion of the housing.

10. The apparatus of claim 1, comprising a magnetic field sensor configured to detect the magnetic field; and
wherein the electrostimulation output circuit is configured to controllably isolate the conductive portion of the housing from the can electrode terminal of the electrostimulation output circuit using the switch in response to information indicative that the magnetic field detected from the magnetic field sensor is in excess of the specified threshold.

11. The apparatus of claim 1, wherein the electrostimulation output circuit is configured to controllably isolate the conductive portion of the housing from the can electrode terminal of the electrostimulation output circuit in response to a command received from an external assembly in communication with the implantable medical device.

12. The apparatus of claim 1, wherein the implantable medical device is configured to operate in one of an MRI mode or an ambulatory mode, and wherein:

the switch is configured to electrically isolate the conductive portion of the housing from the can electrode terminal when the implantable medical device operates in the MRI mode; and
the switch is configured to electrically connect the conductive portion of the housing to the can electrode terminal when the implantable medical device operates in the ambulatory mode.

13. The apparatus of claim 1, wherein the programmable switch control signal generator circuit is configured to generate a control signal in response to a user-programmed MRI mode prior to MRI scanning of a patient.

14. The apparatus of claim 10, wherein the magnetic field sensor is configured to detect the magnetic field including a magnetic resonance imaging (MRI) field, and wherein the electrostimulation output circuit is configured to controllably isolate the conductive portion of the housing from the can electrode terminal using the switch in response to the detected MRI field exceeding a specified threshold.

15. The apparatus of claim 10, wherein the magnetic field sensor is configured to detect the magnetic field including an external magnetic field, and wherein the electrostimulation output circuit is configured to controllably isolate the conductive portion of the housing from the can electrode terminal using the switch in response to the detected external magnetic field exceeding a specified threshold.

16. The apparatus of claim 10, wherein the magnetic field sensor includes a Hall effect sensor.

17. The apparatus of claim 10, wherein the magnetic field sensor includes an inductor saturation detector.

18. The apparatus of claim 1, wherein the programmable switch control signal generator circuit is configured to generate a control signal in response to a diminish of the magnetic field.

19. The apparatus of claim 10, wherein the magnetic field sensor is configured to detect a reduction of the magnetic field, and the implantable medical device is configured to revert from an MRI mode of operation to an ambulatory mode of operation in response to the detected reduction of the magnetic field.

20. An implantable medical device comprising:
an implantable housing including a conductive portion;
an implantable electrostimulation output circuit located within the housing, the electrostimulation output circuit including:
one or more reference voltages coupled to a respective diode;
a can electrode terminal configured to be controllably connected to the conductive portion of the housing, the can electrode terminal configured to be connected to the one or more reference voltages each via the respective diode; and
a programmable switch control signal generator circuit configured to generate a control signal in response to one or more of a user-programmed MRI mode or in response to a detected magnetic field in excess of a specified threshold and to output the control signal using a switch control output; and
a switch comprising two transistors electrically coupled in a series configuration, the switch physically separate from the electrostimulation output circuit and located within the housing, and electrically coupled between the can electrode terminal and the conductive portion of the housing, the switch configured to controllably electrically isolate the conductive portion of the housing from the can electrode terminal of the electrostimulation output circuit in response to the control signal provided by the switch control output;
wherein the electrostimulation output circuit includes a substrate;
wherein each transistor includes a respective substrate, and wherein the respective substrates of the transistors are respectively electrically isolated from the electrostimulation output circuit substrate, and from each other.

* * * * *